United States Patent [19]

Rei et al.

[11] Patent Number: 5,554,635
[45] Date of Patent: Sep. 10, 1996

[54] LIQUID ISOTHIAZOLINONE CONCENTRATES HAVING IMPROVED LOW TEMPERATURE-STABILITY AND IMPROVED ANTI-BACTERIAL PROPERTIES

[75] Inventors: Nuno M. Rei, Boxford; Roger G. Hamel, Methuen, both of Mass.

[73] Assignee: Morton International, Inc., Chicago, Ill.

[21] Appl. No.: 384,883

[22] Filed: Feb. 7, 1995

[51] Int. Cl.$^6$ .................. C07D 275/03; A61K 31/425
[52] U.S. Cl. .......................................... 514/372; 548/213
[58] Field of Search ............................. 514/372; 548/213

[56] References Cited

U.S. PATENT DOCUMENTS

| | | | |
|---|---|---|---|
| 3,360,431 | 12/1967 | Yeager | 167/30 |
| 3,506,720 | 4/1970 | Ernst et al. | 260/613 |
| 4,173,643 | 11/1979 | Law | 424/270 |
| 4,490,280 | 12/1984 | Joshi et al. | 252/368 |
| 4,663,077 | 5/1987 | Rei et al. | 252/364 |
| 4,761,247 | 8/1988 | Rei et al. | 252/364 |
| 5,229,124 | 7/1993 | Rei et al. | 424/409 |

FOREIGN PATENT DOCUMENTS 0364159  4/1990  European Pat. Off. .

OTHER PUBLICATIONS

The Merk Index, 11 ed, Merk and Co., Inc., Rahway N.J., 1989.

Diehl, Karl–Heinz, Seifen, Oele, Fetle, Wachse (1985), 111(8) 222–227.

Voets, J. P., et al., J. Appl. Bact. (1976), 40, 67–72.

Primary Examiner—Johann Richter
Assistant Examiner—Laura R. Cross
Attorney, Agent, or Firm—Wayne E. Nacker; Gerald K. White

[57] ABSTRACT

A liquid concentrate comprises between about 4 and about 10 wt % of an isothiazolinone compound or mixture of isothiazolinone compounds, between about 25 and about 92 wt % of a plasticizer in which said isothiazolinone compound is soluble and between about 4 and about 50 wt % of 2,4,4'-trichloro-2'-hydroxydiphenyl ether. The 2,4,4'-trichloro-2'-hydroxydiphenyl ether stabilizes the concentrate against crystallization and/or freezing at sub-freezing conditions, particularly when the isothiazolinone compound has a melting point of 30° C. or above. 2,4,4'-trichloro-2'-hydroxydiphenyl ether also enhances the anti-microbial properties of an isothiazolinone-containing concentrate.

5 Claims, No Drawings

LIQUID ISOTHIAZOLINONE CONCENTRATES HAVING IMPROVED LOW TEMPERATURE-STABILITY AND IMPROVED ANTI-BACTERIAL PROPERTIES

The present invention is directed to liquid concentrates of isothiazolinones which are stable to crystallization or freezing at sub-freezing temperatures and which have improved anti-microbial properties, particularly with respect to bacteria.

BACKGROUND OF THE INVENTION

It is well known to add biocides to thermoplastic resin compositions to protect articles formed from such compositions against microbial degradation. For processing reasons, it is known to provide biocides as concentrates, such as liquid concentrates as taught, for example, in U.S. Pat. No. 4,758,609, or solid concentrates as taught, for example, in U.S. Pat. No. 4,086,297, the teachings of each of which are incorporated herein by reference. Although a number of biocides have been suggested for use in thermoplastic resins, including isothiazolinones, the standard anti-microbial agent in the industry has been and remains 10,10'-oxybisphenoxarsine (OBPA). While OBPA has proven to be a very effective biocide for use in the plastics industry, there is perceived an eventual need to replace OBPA due to its heavy metal (arsenic) content.

Isothiazolinone compounds are one class of biocides considered to be effective replacements for OBPA and similar heavy metal-containing biocides. At room temperature, some isothiazolinone compounds are in solid form and therefore difficult to handle. Accordingly, isothiazolinone concentrates, including liquid concentrates, have been prepared.

The carrier for a liquid concentrate preferably is a liquid that also has a function in the end-use resin composition to which the concentrate is added to provide anti-microbial properties, and typically in liquid concentrates the carrier is a plasticizer for the end-use resin composition. A problem with concentrates of isothiazolinone-in-plasticizer concentrates wherein the isothiazolinone is present in amounts of greater than about 4 wt %, particularly in amounts of about 10 wt % or greater, is that in sub-freezing conditions which the concentrate may encounter if shipped or stored in winter, the isothiazolinone compounds tend to crystallize from solution or the entire solution tends to freeze. This problem is especially severe with isothiazolinone compounds having melting points of 30° C. or above. This is a significant inconvenience for the plastic processor who must wait for the isothiazolinone to redissolve or the concentrate to thaw and then make sure that the concentrate is homogeneous.

The anti-microbial spectra of some isothiazolinones is less than would be desirable, isothiazolinones tending to be more effective against fungi than bacteria.

It is a general object of the invention to enhance the anti-microbial spectra of isothiazolinone-containing concentrates.

It is another general object of the present invention to provide isothiazolinone compound-in-plasticizer concentrates which contain an isothiazolinone compund, but which concentrates are nevertheless stable to crystallization and/or freezing in winter shipping or storage conditions.

SUMMARY OF THE INVENTION

A liquid concentrate comprises between about 4 and about 25, preferably at least about 10 wt %, of an isothiazolinone compound or mixture of isothiazolinone compounds, between about 25 and about 92 wt % of a plasticizer in which said isothiazolinone compound is soluble, and between about 4 and about 50 wt % of 2,4,4'-trichloro-2'-hydroxydiphenyl ether. When the isothiazolinone is present at at least 4 wt %, the 2,4,4'-trichloro-2'-hydroxydiphenyl ether stabilizes the concentrate against crystallization and/or freezing at sub-freezing conditions. Also, 2,4,4'-trichloro-2'-hydroxydiphenyl ether exhibits anti-bacterial properties, enhancing the anti-microbial properties of an isothiazolinone-containing concentrate.

DETAILED DESCRIPTION OF CERTAIN PREFERRED EMBODIMENTS

Herein, it is to be understood that when any class of compound is discussed in the singular, unless otherwise indicated, a mixture of such compounds may be used instead. Thus when the term "isothiazolinone compound" is used in the singular, a mixture of "isothiazolinone compounds" is within the scope of the invention; and when the term "plasticizer" is used, it is to be understood that a mixture of "plasticizers" would be in accordance with the invention. For example, a mixture of 5-chloro-2-methyl-4-isothiazolin-3-one and 2-methyl-4-isothiazolin-3-one is sold commercially as RH 886; this mixture being within the scope of the invention.

Generally any plasticizer in which the isothiazolinone compound is soluble is suitable for use in the present invention. Examples of such plasticizers include, but are not limited to tricresyl phosphate, dipropylene glycol dibenzoate, diphenylcresyl phosphate, dipropylene glycol dibenzoate, diphenylcresyl phosphate, epoxidized soya, epoxidized tallate, dioctyl azelate, di(2-ethyl hexyl)phthalate, alkyl aryl phosphates, diisobutyl phthalate, diisodecyl phthalate, hydrogenated methyl rosin ester, n-octyl n-decyl phthalate, mixed n-alkyl phthalates, butyl benzyl phthalate, di-n-octyl phthalate, di-n-decyl phthalate, 3,4-epoxycyclohexyl methyl 3,4-epoxycyclohexane carboxylate, trioctyl trimellitate and low molecular wight polymeric plasticizers such as Paraplex® G-30 plasticizer sold by Rohm & Haas Co. and the like. Of these plasticizers, di(2-ethyl hexyl) phthalate, diisodecyl phthalate, butyl benzyl phthalate and epoxidized soya are preferred.

The isothiazolinone compounds useful in this invention include those described in U.S. Pat. Nos. 3,523,121 (issued Aug. 4, 1970); 3,761,488 (issued Sep. 25, 1973) and 4,105,431 (issued Aug. 8, 1978). The isothiazolinone compounds described in these patents have the structural formula:

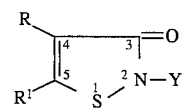

wherein Y is alkyl of 1 to 18 carbon atoms, cycloalkyl of 3 to 6 carbon atoms; aralkyl of up to 10 carbon atoms; halogen, lower alkyl, or lower alkoxy substituted aralkyl of up to 10 carbon atoms; aryl; halogen, nitro, lower alkyl, lower alkylacylamino, lower carbalkoxy or sulfamyl substituted aryl; lower hydroxyalkyl; lower haloalkyl; lower dialkylaminoalkyl; or a carbamoyl group having the structure

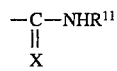

When Y is any of the above substituents other than the carbamoyl group, then R and R' may be hydrogen, halogen or lower alkyl.

When Y is the carbamoyl group, then R may be hydrogen, lower alkyl, halogen or cyano;

R' may be hydrogen, halogen, lower alkyl or lower haloalkyl when R is hydrogen, lower alkyl or halogen;

R' may be lower alkylthio, lower alkylsulfinyl or lower alkylsulfonyl when R is cyano;

X may be oxygen or sulfur; and

R'' may be alkyl of 1 to 18 carbon atoms, lower alkylsulfonyl, arylsulfonyl, halogen or lower alkyl substituted arylsulfonyl, or aryl group of the formula

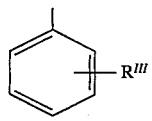

wherein $R^{III}$ may be lower alkyl, halogen, nitro of alkoxy of 1 to 4 carbon atoms.

Where the expression "lower" is employed in conjunction with terms, such as alkyl, haloalkyl, alkylthio, alkylsulfinyl, alkylsulfonyl, etc., it is intended to indicate that the alkyl or alkyl portion thereof has a carbon content of 1 to 4 carbon atoms. Typically, the alkyl or alkyl portion may be methyl, ethyl, propyl, isopropyl, butyl, t-butyl and the like.

Some of the isothiazolinones described above can form novel acid salts which also exhibit biocidal activity. Such salt forming compounds fall within the scope of the above formula wherein Y is alkyl of 1 to 18 carbon atoms; cycloalkyl of 3 of 6 carbon atoms; aralkyl of up to 10 carbon atoms; halogen lower alkyl, or lower alkoxy substituted aralkyl of up to 10 carbon atoms; aryl; halogen, nitro, lower alkyl, lower alkylacylamino, lower carbalkoxy or sulfamyl substituted aryl; lower hydroxyalkyl; lower haloalkyl; or lower dialkylaminoalkyl; and R and R' are selected from the group consisting of hydrogen, lower alkyl, or halogen. Examples of preferred isothiazolinone compounds useful in this invention include 2-(n-octyl-4-isothiazolin-3-one), 4,5-dichloro-2-cyclohexyl-3-isothiazolinone, 4,5-dichloro-2-(n-octyl-4-isothiazolin-3-one)

5-chloro-2-methyl-4-isothiazolin-3-one, 2-methyl-4-isothiazolin-3-one, and mixtures thereof.

Of those listed above, 4,5-dichloro-2-(n-octyl-4-isothiazolin-3-one) is of particular interest because it exhibits good weathering characteristics, important for outside applications. However, because its melting point is above 40° C., concentrates tend to exhibit poor low temperature stability. 2,4,4'-trichloro-2'-hydroxydiphenyl ether enhances the low temperature stability of concentrates containing this compound.

While some isothiazolinone compounds are very effective fungicides, they tend to have less effectiveness against many bacteria. The 2,4,4'-trichloro-2'-hydroxydiphenyl ether itself has anti-microbial properties, thereby enhancing the antibacterial properties of the concentrate as a whole. 2,4,4'-trichloro-2'-hydroxydiphenyl ether is sold as Irgasan® DP 300 by Ciba-Geigy Corp.

It is also within the scope of this invention to use mixtures of biocides that include an isothiazolinone and another biocide. For example, a product sold as Vinzene® BP 4081 is a mixture of an isothiazolinone and OBPA.

The invention will now be described in greater detail by way of specific examples.

EXAMPLES 1–5

Samples with various amounts of 4,5-dichloro-2-(n-octyl-4-isothiazolin-3-one) (RH 287), plasticizer and 2,4,4'-trichloro-2'-hydroxydiphenyl ether (DP 300) were exposed to temperatures of 0° F. (−18° C.) for 48 hours and the samples then observed. Compositions (components in wt %; plasticizer=balance) and results are as follows:

| Example | RH287 | Plasticizer | DP 300 | Comments |
|---------|-------|-------------|--------|----------|
| 1 | 5 | DOP | 0 | OK |
| 2 | 10 | DOP | 0 | Frozen |
| 3 | 10 | DOP | 10 | Some solid |
| 4 | 20 | DOP | 40 | OK, viscous |
| 5 | 10 | DOP | 20 | OK |

DOP = di 2-ethyl hexyl phthalate

EXAMPLES 6–17

Samples with various amounts of RH 287 were subjected to five freeze/thaw cycles. In the freeze cycles the samples were left in the freezer at 0° F. (−18° C.) for two to five days. The thaw cycle was at room temperature for at least one day. Compositions (components in wt %; plasticizer=balance) and results are as follows:

| Example | RH287 | Plasticizer | DP300 | Comments |
|---------|-------|-------------|-------|----------|
| 6 | 5 | S 711 | 0 | 3 cycles OK; 2 cycles, 1 small crystal |
| 7 | 10 | S 711 | 0 | Solid |
| 8 | 10 | S 711 | 10 | OK |
| 9 | 10 | S 711 | 20 | OK |
| 10 | 10 | S 711 | 25 | OK |
| 11 | 15 | S 711 | 0 | Solid |
| 12 | 20 | S 711 | 40 | OK |
| 13 | 10 | DIDP | 0 | Solid |
| 14 | 10 | DIDP | 10 | OK |
| 15 | 10 | DIDP | 20 | OK |
| 16 | 10 | DIDP | 25 | OK |
| 17 | 20 | DIDP | 40 | OK |

S 711 = predominantly straight chain phthalate ester
DIDP = diisodecylphthalate

What is claimed is:

1. A liquid concentrate comprising between about 4 and about 25 wt % of an isothiazolinone compound or mixture of isothiazolinone compounds, between about 25 and about 92 wt % of a plasticizer in which said isothiazolinone compound or mixture of isothiazolinone compounds is soluble and between about 4 and about 50 wt % of 2,4,4'-trichloro-2'-hydroxydiphenyl ether.

2. A liquid concentrate according to claim 1 wherein said concentrate comprises at least 4 wt % of an isothiazolinone compound having a melting point of at least 30° C.

3. A liquid concentrate according to claim 1 wherein said concentrate comprises at least 10 wt % of an isothiazolinone compound or mixture of isothiazolinone compounds having a melting point of at least 30° C.

4. A liquid concentrate comprising between about 4 and about 25 wt % of an isothiazolinone compound or mixture of isothiazolinone compounds selected from the group consisting of 2-(n-octyl-4-isothiazolin-3-one), 4,5-dichloro-2-cyclohexyl-3-isothiazolinone, 4,5-dichloro-2-(n-octyl-4-isothiazolin-3-one), 5-chloro-2-methyl-4-isothiazolin-3-one, 2-methyl-4-isothiazolin-3-one, and mixtures thereof, between about 25 and about 92 wt % of a plasticizer in which said isothiazolinone compound or mixture of isothiazolinone compounds is soluble and between about 4 and about 50 wt % of 2,4,4'-trichloro-2'-hydroxydiphenyl ether.

5. A liquid concentrate comprising between about 4 and about 25 wt % of 4,5-dichloro-2-(n-octyl-4-isothiazolin-3-one), between about 25 and about 92 wt % of a plasticizer in which said 4,5-dichloro-2-(n-octyl-4-isothiazolin-3-one) is soluble and between about 4 and about 50 wt % of 2,4,4'-trichloro-2'-hydroxydiphenyl ether.

* * * * *